United States Patent [19]

Knifton

[11] Patent Number: 4,568,780

[45] Date of Patent: Feb. 4, 1986

[54] PROCESS FOR LOW PRESSURE SYNTHESIS OF ETHYLENE GLYCOL FROM SYNTHESIS GAS PLUS 1,3-DIOXOLANE

[75] Inventor: John F. Knifton, Austin, Tex.

[73] Assignee: Texaco Inc., White Plains, N.Y.

[21] Appl. No.: 663,280

[22] Filed: Oct. 22, 1984

[51] Int. Cl.$^4$ .................. C07C 29/00; C07C 31/20
[52] U.S. Cl. ............................ 568/866; 568/678; 568/680; 568/881
[58] Field of Search ..................................... 568/866

[56] References Cited

U.S. PATENT DOCUMENTS 2,421,862  6/1947  Arundale et al. .................... 568/866
4,356,332  10/1982  Knifton ................................ 568/852

Primary Examiner—J. E. Evans
Attorney, Agent, or Firm—Jack H. Park; Kenneth R. Priem; Cynthia L. Kendrick

[57] ABSTRACT

This invention relates to the manufacture of ethylene glycol and more particularly to a low pressure process for making ethylene glycol comprising reacting synthesis gas, i.e. a mixture of carbon monoxide and hydrogen, plus 1,3-dioxolane in the presence of a homogenous liquid catalyst containing an effective amount of cobalt-containing compound and a silane or germane-containing promoter dispersed in a hydrocarbon solvent at a temperature of at least 50° C. and a pressure of at least 500 psi, where the particular solvents used allow the desired product to be separated from the reaction mixture by phase separation.

12 Claims, No Drawings

PROCESS FOR LOW PRESSURE SYNTHESIS OF ETHYLENE GLYCOL FROM SYNTHESIS GAS PLUS 1,3-DIOXOLANE

This application is related to copending U.S. patent application Ser. Nos. 663,281, 663,284 and 663,602, filed of even date.

FIELD OF THE INVENTION

This invention relates to a new process for preparing ethylene glycol. More particularly, this invention relates to a novel process for preparing ethylene glycol in high yields from syngas which comprises contacting syngas, (a mixture of carbon monoxide and hydrogen), plus 1,3-dioxolane with a catalyst comprising a cobalt-containing compound and a silane or germane promoter dispersed in a hydrocarbon solvent at a temperature of at least 50° C. and a moderate pressure of at least 500 psig.

BACKGROUND OF THE INVENTION

Ethylene glycol is a chemical which has found wide use in industry. It is used, for example in the preparation of plasticizers for vinyl polymers and as a component in polyester fibers and antifreeze formulations. In view of its many uses, there is a need to find new and more economical methods for preparing ethylene glycol.

Proposed methods for making ethylene glycol involve the reaction of carbon monoxide with hydrogen in the presence of various proposed catalyst systems at elevated temperatures and pressures. For example, one of the earliest disclosed processes for making polyhydroxy compounds from readily available and inexpensive starting materials such as formaldehyde, carbon monoxide and hydrogen was disclosed in U.S. Pat. No. 2,451,333. The process comprised heating the starting materials with a reduced cobalt oxide hydrogenation catalyst under a high pressure, in excess of 100 atm. and at a temperature from about 80° C. to 300° C. Actually the examples in this patent used high pressures in the range of 500-800 atmospheres.

In Japan Kokai No. 76,128,903 (1976) to Mitsubishi a procedure is disclosed for preparing ethylene glycol by the reaction of CO, $H_2$ and HCHO with a cobalt catalyst containing a trivalent P, As or Sb compound at a temperature of about 160° C. and a pressure of about 180 Kg/cm$^2$, or approximately 2700 psi.

Similarly U.S. Pat. No. 4,144,401 uses CO, $H_2$ and formaldehyde as starting materials, but they are reacted in the presence of an alcohol solvent and a catalytic amount of rhodium or a rhodium-containing compound at a moderate temperature and pressure. Of course use of rhodium in a catalyst makes it expensive for commercial purposes. Methanol is also produced in substantial amounts in this process.

U.S. Pat. No. 4,356,332 pertains to the production of ethylene glycol by reaction of formaldehyde with carbon monoxide and hydrogen in the presence of a catalyst comprising a cobalt-containing compound and a tin-or germanium-containing promoter and in the presence of a substantially inert, oxygenated hydrocarbon solvent.

In U.S. Pat. No. 4,200,765 there is disclosed a process for preparing glycol aldehyde by reacting formaldehyde, hydrogen and carbon monoxide in an aprotic solvent at elevated temperatures and superatmospheric pressures in the presence of a rhodium catalyst with subsequent conversion of the glycol aldehyde to ethylene glycol by hydrogenation.

Japan Kokai No. 82,118,527 (1981) to Mitsubishi discloses the use of a ruthenium-based catalyst with a trivalent phosphorous compound to convert formaldehyde, CO and $H_2$ into ethylene glycol. The selectivity to ethylene glycol is not specified.

Japan Kokai No. 82,130,940 (1981) to Mitsui Petrochemicals employs a rhodium compound and an alkali metal compound. Again selectivity to ethylene glycol is not specified.

In U.S. Pat. No. 4,367,820 only carbon monoxide and hydrogen, without formaldehyde are used as starting materials for conversion to ethylene glycol via a catalyst comprising a cobalt-containing compound and a large excess of organosilicon compound. In most of the examples an operating temperature range of 250°-270° C. is employed, coupled with pressures of about 4000-8000 psi. Weight ratios of ethylene glycol to methanol were typically Ca. 2:1.

Additional Japanese applications disclose the use of a solution of formalin, carbon monoxide and hydrogen to produce ethylene glycol in the presence of a cobalt catalyst. See Japanese Application No. 197909 to Agency of Ind. Sci. Tech. In Jap. Application No. 188137 to the same agency, ethylene glycol is produced by reacting CO and hydrogen optionally with formaldehyde in the presence of a cobalt carbonyl and a phenol and/or alkylphenol.

Japanese Application No. 004782 (1981) to Mitsubishi discloses a process for producing ethylene glycol from formaldehyde, CO and $H_2$ in the presence of a catalyst containing ruthenium and a trivalent organo-phosphorous compound.

Finally in Japan Kokai Tokyo Koho JP No. 57,130,933 to Mitsubishi, acetals are reacted with CO and $H_2$ in the presence of a cobalt-iodine catalyst system to produce ethylene glycol.

Many of these processes require the use of high pressures (particularly in the absence of an added formaldehyde source), some use expensive rhodium-containing compounds and in most the selectivities for ethylene glycol are not very substantial and separation of the desired product is difficult.

The disclosure of a process for producing ethylene glycol from simple starting materials such as syngas (i.e. carbon monoxide and hydrogen) and 1,3-dioxolane by reacting the starting materials in the presence of a catalyst compound which would be relatively inexpensive, even on a commercial sale, and which could be reacted at low temperatures and pressures therefore allowing for less expense in construction of reactors, etc. would be an advance in the art, especially if the selectivity for ethylene glycol were better than found in previous work. Further, it would be a considerable advance in the art if the desired product could be obtained from the reaction mixture by a simple phase separation technique.

SUMMARY OF THE INVENTION

This invention concerns a process for making ethylene glycol comprising contacting a mixture of synthesis gas, i.e., carbon monoxide and hydrogen, plus 1,3-dioxolane with a catalyst comprising a cobalt-containing compound and a silane or germane-containing compound and heating the resultant mixture at a temperature of at least 50° C. and a pressure of at least 500 psi and preferably less than 5000 psi for sufficient time to produce the desired ethylene glycol. By using this catalyst system one can obtain high yields of ethylene glycol, the process can be operated at lower temperatures and pressures and the use of extreme conditions and expensive catalyst compounds required in many of the prior known processes can be avoided. Also, the process provides for ease of separation of the glycol products from the selected solvent. This results because, for example, where 1,2,4-trichlorobenzene is used as a solvent, the glycol products separate as an aqueous rich phase.

The process of the invention, as far as the formation of the desired ethylene glycol is concerned, may be represented by the following equation:

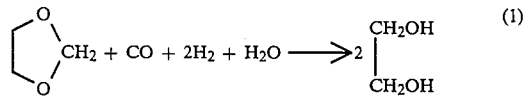 (1)

Typical concentrations of ethylene glycol in the crude liquid product range up to 60 wt % of the phase which separates, typical yields of ethylene glycol (basis 1,3-dioxolane charged) range up to 50 mole %. Total glycol products may comprise up to greater than 65 wt % of the crude liquid product phase.

A further advantage of this process is that there appears to be no competing water-gas shift or methanation activity with this class of solvent solubilized cobalt-silane or cobalt-germane catalyst. Ethylene glycol/methanol ratios in the crude liquid product may exceed 25:1.

DETAILED DESCRIPTION OF THE INVENTION

In the operation of the process of the invention, ethylene glycol is prepared from a synthesis gas mixture of carbon monoxide and hydrogen plus 1,3-dioxolane by a process comprising the following steps:
(a) contacting said mixture of carbon monoxide, hydrogen and 1,3-dioxolane with a catalyst comprising a cobalt-containing compound and a silane or germane-containing compound dispersed in a solvent selected from the group including halogen-containing aromatic and hydrocarbyl ether solvents, said solvent allowing separation of glycol products from the main body of the solvent,
(b) heating said mixture to a temperature of at least 50° C. under a pressure greater than 500 psi with sufficient carbon monoxide and hydrogen to satisfy the above-noted stoichiometry of the desired ethylene glycol synthesis until substantial formation of the desired ethylene glycol has been achieved; and
(c) preferably isolating said ethylene glycol by separation of an aqueous-rich phase from the main body of the selected solvent.

In order to present the inventive concept of the present invention in the greatest possible detail, the following supplementary disclosure is submitted. The process of the invention is practiced as follows:

As noted, the new catalyst system used in the process of the invention contains a cobalt-containing compound and a silane or germane-containing promoter. The cobalt compound to be used may be chosen from a wide variety of organic and inorganic compounds, complexes, etc. It is only necessary that the catalyst employed contain the cobalt in any of its ionic states.

The cobalt-containing compound employed may take many different forms. For instance the cobalt may be added to the reaction mixture in an oxide form as in the case of, for example, cobalt(II) oxide, (CoO) or cobalt-(II,III) oxide (Co$_3$O$_4$). Alternatively, it may be added as the salt of a mineral acid, as in case of cobalt(II) nitrate hydrate (Co(NO$_3$)$_2$.6H$_2$O), cobalt(II) phosphate, cobalt(II) sulfate, etc. or as the salt of a suitable organic carboxylic acid, for example, cobalt(II) formate, cobalt-(II) acetate, cobalt(II) propionate, cobalt naphthenate, or bonded to a carbonyl-containing ligand as in the case of cobalt acetylacetonate, etc. The cobalt may also be added to the reaction zone as a carbonyl or hydridocarbonyl derivative. Here, suitable examples include dicobalt octacarbonyl, (Co$_2$(CO)$_8$), cobalt hydridocarbonyl, (HCo(CO)$_4$) and substituted carbonyl species such as the organophosphorus cobalt carbonyls like HCo(CO)$_3$-(Bu$_3$P).

Preferred cobalt-containing compounds include oxides of cobalt, cobalt salts of mineral acids, cobalt salts of organic carboxylic acids and cobalt carbonyl or hydridocarbonyl derivatives. Among these, particularly preferred are dicobalt octacarbonyl, cobalt(II) oxide, cobalt(II) nitrate, cobalt acetylacetonate and cobalt(II) acetate.

The silane or germane-containing promoter employed in the practice of this invention may also take many different forms. Generally, the silicon-containing promoter should contain at least one bond between a silicon atom and a carbon atom, but suitable organosilicon compounds may comprise mono-, di-, tri- and tetraorgano groups bonded to silicon. Each organo group may be an alkyl, aryl or aryalkyl moiety, having one to 20 carbon atoms. The silicon-containing promoter may also contain silicon-oxygen bonds, and preferred promoters are halogen-free silanes containing at least one silicon-hydrogen bond per molecule.

Typical organosilicon compounds that are suitable for use in the process of equation (1) include trialkylsilanes, such as triethylsilane (Et$_3$SiH), tricyclohexylsilane [(C$_6$H$_{11}$)$_3$SiH], trimethylsilane, tri-n-hexylsilane and methyldiethylsilane (MeEt$_2$SiH), as well as dimethylethylsilane and the tripropylsilanes, the dialkylsilanes such as diethylsilane (Et$_2$SiH$_2$) and dimethylsilane, the tetraalkylsilanes such as tetramethylsilane and tetraethylsilane, the arylsilanes such as triphenylsilane (Ph$_3$SiH), diphenylsilane and hydroxytriphenylsilane, as well as the alkoxysilanes such as triethoxysilane [(EtO)$_3$SiH], phenyltriethoxysilane, tetraethoxysilane and tetramethoxysilane. Less satisfactory are the halogenated organosilanes such as chlorotrimethylsilane, dimethylsilane chloride (Me$_2$SiHCl), chlorotriphenylsilane, dichlorodimethylsilane (Me$_2$SiCl$_2$), chlorotriethylsilane, and iodotrimethylsilane. Other suitable organosilicon promoters containing at least one silicon-hydride bond, and more than one silicon atom per molecule, include:
H$_3$SiCH$_2$SiH$_3$
H$_3$SiCH$_2$CH$_2$SiH$_3$
CH$_3$SiH$_2$CH$_2$SiH$_3$

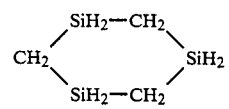

Suitable silanes containing more than one silicon-hydride bond per molecule are exemplified by:

$C_6H_{13}SiH_3$
$CH_3CH=CHCH_2SiH_3$ $$CH_2=CHCHSiH_3 \atop CH_3$$

$CH_2=CHCH_2SiH_3$
$C_6H_5CH_2CH_2SiH_3$
$C_6H_5CH(CH_3)SiH_3$
$(C_3H_7)_2SiH_2$
$(CH_3)(isoC_4H_9)SiH_2$
$(C_2H_5)(isoC_4H_9)SiH_2$
$(CH_2=CH)(C_2H_5)SiH_2$
$(CH_2=CH)(C_4H_9)SiH_2$ Also effective as silicon-containing promoters in the practice of this process are siloxanes and polyalkylsiloxanes. These may include hexaethyldisiloxane, hexamethylcyclotrisiloxane, octamethylcyclotetrasiloxane, hexamethyldisiloxane, tetramethyldisiloxane (Me$_2$HSi-OSiHMe$_2$), methylhydrocyclosiloxane, or the alkylsiloxane polymers of the type:

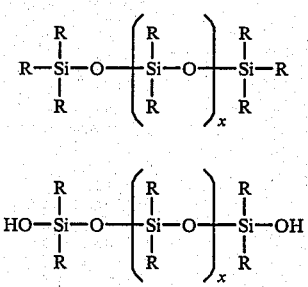

wherein R is one or different alkyl groups containing 1 to 6 carbon atoms.

Equally useful are the higher M.W. tetraalkylsilanes and tetraalkoxysilanes wherein each alkyl or alkoxy group contains 1 to 20 carbon atoms, and each alkyl group may have the same or different carbon number.

Preferred organosilane compounds include triethylsilane, triphenylsilane, trimethylsilane, diphenylsilane, tricyclohexylsilane, tetramethylsilane, tetraethylsilane, hydroxytriphenylsilane, diethylsilane and tripropylsilane.

The germanium-containing compound which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermane, tetraethylgermane, tetraphenylgermane and tetramethylgermane, or an organohalide germanium compound such as diphenylgermanium chloride, methylgermanium trichloride, phenylgermanium trichloride, tri-n-butylgermanium iodide, triethylgermanium chloride, triethylgermanium iodide, trimethylgermanium chloride, triphenylgermanium bromide and triphenylgermanium chloride, or as an organogermanium hydride, such as triphenylgermanium hydride, or as an organogermanium oxide or carboxylate such as triphenylgermanium acetate, or as a germanium alkoxide such as germanium butoxide, germanium ethoxide or germanium methoxide.

The preferred germanium-containing promoter compounds are the organo-halide germanium compounds, the hydrocarbyl germanium compounds, and the organogermanium hydrides. Among these, particularly preferred are triphenylgermanium bromide, trimethylgermanium bromide, triphenylgermanium hydride, tetraphenylgermane, tetraethylgermane and triethylgermanium chloride.

As characterized above, this process is operated as a homogeneous liquid phase mixture. The process is typically carried out in a solvent. The solvent should preferably be a liquid at room temperature but should at least, in part, be a liquid under the conditions of reaction. The solvent is selected such that it is capable of:

(a) Maintaining the cobalt catalyst in the homogeneous liquid phase mixture throughout the synthesis of desired ethylene glycol.

(b) Ensuring good selectivity and yields to desired ethylene glycol and its derivatives.

(c) Achieving separation of the majority of the ethylene glycol product as a separate liquid phase from the cobalt catalyst-rich solvent phase at the completion of the desired glycol synthesis.

Three classes of hydrocarbon solvent are discussed herein that are useful in the process of this invention and which satisfy the criteria described supra; those include halogenated aromatic-containing solvents, hydrocarbyl ether solvents, and aromatic hydrocarbon solvents.

Generally these solvents will contain up to 20 carbon atoms per molecule and preferable a maximum of 4 halogen atoms per molecule. The solvent must be substantially inert under typical Co-hydrogenation conditions that yield glycol products and it must be one which has a normal boiling point of at least 65° C. at atmospheric pressure. Preferably, the solvent will have a boiling point greater than that of methanol and other oxygen-containing reaction products so that recovery of the glycol product by distillation is facilitated.

Suitable halogen-containing solvents that are satisfactory for this glycol process contain up to 20 carbon atoms per molecule and preferably no more than 4 halogen atoms per molecule. They are exemplified by, but not limited to, chlorobenzene, bromobenzene, o-dichlorobenzene, 1,2,4-trichlorobenzene, 1,3,5-tribromobenzene, p-bromotoluene, 2-bromo-m-xylene, α-bromo-p-xylene, 2-chlorobiphenyl, 7-chlorobiphenyl, o-dibromobenzene, 2,2'-dibromobiphenyl, 4,4'-dibromobiphenyl, 2,5-dibromotoluene, 2,4,6-tribromotoluene, 2,3,6-trichlorotoluene, p-xylene dichloride and 1,2,4-trifluorobenzene.

Also effective are aromatic and aliphatic solvents containing the ether linkage. Examples of such solvents include anisole, p-dioxane, ethylene glycol dimethyl ether, tetrahydrofuran, triethyleneglycol dimethyl ether, diphenyl oxide, as well as halogenated ether solvents such as p-bromoanisole, m-chloroanisole, and brominated diphenyl oxide.

Suitable aromatic-type solvents that are satisfactory in the practice of this invention contain 6 to 20 carbon atoms per molecule and at least one aromatic ring moiety per molecule. They are exemplified by, but not limited to, benzene, toluene, p-xylene, o-xylene, m-xylene, mixed xylenes, ethylbenzene, mesitylene, biphenyl, cumene, diethylbenzene, diphenylmethane, dixylyethane, durene, ethyl toluenes, fluorene, naphthalene, n-nonylbenzene, phenyltoluenes, stilbene, tetralin, tetramethylbenzenes, tetraphenylmethane, and n-propylbenzene.

The most effective solvents in terms of (a) glycol concentration in the crude aqueous phase of the liquid product, (b) total glycol product yield and (c) cobalt recovery in solution appear to be halogenated solvents of the group including o-dichlorobenzene, 1,2,4-trichlorobenzene, p-bromoanisole, m-chloroanisole, bromobenzene and dibromobenzene. There appears to be very little competing water-gas shift or methanation activity with this class of solvent-solubilized cobalt-silane or cobalt-germane catalyst. Ethylene glycol/methanol ratios may reach 25:1 or better.

The quantity of cobalt-containing compound and the silane or germane-containing compound to be used in the process of the invention may vary. The process is conducted in the presence of a catalytically effective quantity of the active cobalt-containing compound and the active silane or germane-containing compound which gives the desired product in a reasonable yield. The reaction proceeds when employing as little as about $10^{-2}$ weight percent, and even lesser amounts of the cobalt-containing compound, together with as little as about $10^{-2}$ weight percent of the silane or germane-containing compound based on the total weight of the reaction mixture. The upper concentration is dictated by a variety of factors including catalyst cost, partial pressures of carbon monoxide and hydrogen, operating temperature, etc. A cobalt-containing compound concentration of from about $10^{-2}$ to about 30 weight percent in conjunction with a silane or germane-containing compound concentration of from about $10^{-2}$ to about 50 percent and a solvent concentration of about 10 to 95 percent, based on the total weight of the reaction mixture is generally desirable in the practice of this invention.

Particularly superior results are obtained when the above-noted components of the catalyst system are combined as follows on a molar basis: cobalt-containing compounds to silane or germane-containing compound of 1:0.1 to 1:100.

The temperature range which can be employed in the process of the invention may vary over a considerable range depending upon experimental factors, including the choice of catalyst, pressure and other variables. A preferred range of operability is from about 50° C. to about 350° C. when superatmospheric pressures of syngas are employed. A narrower range of about 100° C. to 220° C. represents a preferred temperature range.

The pressure employed may also vary over a considerable range, but in most cases is at least above 500 psig. A preferred operating range varies from about 1000 psig to about 6000 psig, although pressures above 6000 psig also provide useful yields of the desired product. The pressures referred to herein represent the total pressure generated by all the reactants, although they are substantially due to the carbon monoxide and hydrogen fractions. In the presence of 1,3-dioxolane, the total pressures required for glycol syntheses using cobalt/silane or germane-promoted catalyst systems are normally lower than those pressures required for direct glycol production from $CO/H_2$ (See, for example, U.S. Pat. No. 4,367,820).

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether and alkanols, such as methanol.

In all these synthesis in order to achieve a high degree of selectivity the amount of carbon monoxide, hydrogen and 1,3-dioxolane present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The most desired product of this synthesis, ethylene glycol (EG) will be formed in significant quantities (up to Ca. 60 wt % concentration in the crude liquid product) and up to Ca. 50 mole % yield (basis total 1,3-dioxolane charged) using the cobalt-silane or germane promoted catalyst system of this invention. Also formed are significant amounts of diethylene glycol (DEG), propylene glycol (PG), together with derivatives such as the ethylene glycol monoalkyl ethers (e.g. ethylene glycol monomethyl ether, EGMME). Selectivity to total glycol products (EG+DEG+PG+EGMME) may exceed 65 wt %. Lower monohydric alcohols such as methanol and ethanol are also present in the crude liquid product mix. Each of these oxygenated products including ethylene glycol, monohydric alcohols and other by-products can be recovered from the reaction mixture by conventional means, e.g. fractional distillation in vacuo. However, when halogenated aromatics and hydrocarbyl ethers are used as the solvent, the products can be separated by a simple phase separation technique.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch gauge (psig).

The yield of ethylene glycol in each synthesis (mole %) is estimated basis equation 1 using the formula:

$$\frac{\text{Total Ethylene Glycol Produced mmole)}}{[\text{Total 1,3-dioxolane charged (mmole)}] \times 2} \times 100$$

Total liquid product increase (wt %) is estimated basis:

$$\frac{(\text{Total Liquid} + \text{Solid Product, g}) - (\text{Total Catalyst} + \text{Solvent} + \text{1,3-dioxolane charged, g})}{(\text{Total Catalyst} + \text{Solvent} + \text{1,3-Dioxolane Charged, g})} \times 100$$

To illustrate the process of the invention, the following examples are given. It will be apparent from the examples that ethylene glycol synthesis in good yields has been demonstrated over a broad range of operating temperatures. It is to be understood, however, that the examples are given in the way of illustration and are not to be regarded as limiting the invention in any way.

EXAMPLE I

A 450 ml capacity reactor with glass liner was charged with a mixture of dicobalt octacarbonyl (12.0 mmole Co, 2.052 g), triethylsilane (24.0 mmole Si, 2.790 g) and 1,3-dioxolane (200 mmole, 14.82 g), water (200 mmole, 3.60 g) and 1,2,4-trichlorobenzene (15.0 g). The mixture was flushed with nitrogen, the reactor sealed, flushed with synthesis gas, pressured to 2700 psig with $CO/H_2$ (1:2), and heated to 160° C. with agitation. After four hours, the reactor was allowed to cool, the gas pressure (2300 psig) noted, and the excess gas sampled and vented. 41.9 g of two-phase liquid product was recovered, there was no solid precipitate at this stage.

Analysis (glc) of the less dense liquid phase (20 ml) shows it to contain:
50.9 wt % ethylene glycol (EG)
3.4 wt % ethylene glycol monomethyl ether (EGMME)
0.7 wt % propylene glycol (PG)
3.2 wt % diethylene glycol (DEG)
1.8 wt % methanol
0.1 wt % ethanol
1.2 wt % 1,2,4-trichlorobenzene
20.4 wt % water.

Analysis (glc) of the heavier liquid phase (15 ml) shows it to contain:
91.4 wt % 1,2,4-trichlorobenzene
0.3 wt % ethylene glycol
0.2 wt % ethylene glycol monomethyl ether
8.1 wt % unidentified material.

Analysis of the gas sample shows it to contain:
64% hydrogen
24% carbon monoxide
<0.1% carbon dioxide
<0.1% methane.

Estimated yield of ethylene glycol is 174 mmole.
The estimated yield of ethylene glycol (basis 1,3-dioxolane charged) is 44 mole %.
The estimated liquid yield increase is 9.4 wt %.

EXAMPLES II–XIII

Examples II–XIII were conducted in the same way as Example I. In every example dicobalt octacarbonyl was the cobalt-containing catalyst used and 1,2,4-trichlorobenzene was employed as the solvent. The promoter used was triethylsilane, $Et_3SiH$, and the results in terms of weight percent of ethylene glycol, propylene glycol, diethylene glycol, glycol monomethyl ether etc. in the crude liquid product are shown in Table I.

It may be seen from an inspection of Table I that:

(a) Ethylene glycol is the predominant product fraction in many of these runs.

In Run VIII, for example, the aqueous-glycol phase of the product fraction comprises:
59.2 wt % ethylene glycol, and
69.1 wt % total EG+PG+DEG+EGMME.

Likewise, in Example III, the aqueous-glycol phase comprised:
61.8 wt % ethylene glycol and
65.5 wt % total EG+PG+DEG+EGMME.

(b) Glycol synthesis has been demonstrated over a broad range of operating temperatures, pressures and 1,3-dioxolane/cobalt molar ratios.

TABLE I

SYNTHESIS OF ETHYLENE GLYCOL FROM SYNGAS PLUS 1,3-DIOXOLANE[a]

| Example | 1,3-dioxolane (mmole) | Water (mmole) | Temp (°C.) | Pres. (psig) | H₂O | MeOH | EtOH | EGMME | EG | PG | DEG | Solvent | Dioxolane |
|---|---|---|---|---|---|---|---|---|---|---|---|---|---|
| II | 200 | 200 | 160 | 2000 | 17.3 | 4.2 | 0.1 | 5.7 | 50.9 | 0.3 | 1.7 | 5.3 | 0.6 |
|  |  |  |  |  | 0.2 | 0.2 |  | 0.4 | — | 0.1 | 1.6 | 91 | 0.6 |
| III | 200 | 200 | 160 | 1000 | 14.9 | 4.0 |  | 3.2 | 61.8 | 0.3 | 0.2 | 1.3 | 6.1 |
|  |  |  |  |  | 0.1 | 0.2 |  | 0.2 | 0.2 |  | 0.5 | 86 | 79 |
| IV | 200 | 200 | 160 | 500 | 27.7 | 1.0 | 0.1 | 0.3 | 32.6 |  |  | 11.7 | 26.0 |
|  |  |  |  |  | 0.1 | 0.2 |  |  | 0.2 |  | 0.3 | 53.7 | 38.6 |
| V | 200 | 200 | 140 | 2000 | 23.2 | 1.6 |  | 2.5 | 47.9 | 0.4 | 1.3 | 2.2 | 5.8 |
|  |  |  |  |  |  |  |  | 0.2 |  |  | 0.2 | 89.8 | 6.0 |
| VI | 200 | 200 | 120 | 2000 | 26.0 | 0.4 |  | 0.8 | 30.0 | 0.6 | 0.6 | 2.4 | 20.9 |
|  |  |  |  |  |  |  |  | 0.1 | 0.1 |  |  | 70.5 | 19.4 |
| VII | 200 | 200 | 100 | 2000 | 32.3 | 0.1 |  | 0.2 | 17.6 | 0.2 |  | 1.5 | 37.0 |
|  |  |  |  |  | 0.6 | 0.1 |  | 0.2 |  | 0.1 | 0.1 | 57.8 | 38.9 |
| VIII | 200 | 200 | 180 | 2000 | 17.4 | 7.5 | 0.4 | 7.8 | 59.2 | 0.2 | 1.9 | 1.6 | — |
|  |  |  |  |  | 0.4 | 0.4 |  | 0.7 | 0.5 |  | 2.7 | 87.8 | 0.1 |
| IX | 200 | 200 | 200 | 2000 | 19.6 | 7.7 |  | 3.2 | 49.8 | 0.3 | 0.7 | 1.6 | 11.0 |
|  |  |  |  |  | 0.2 | 1.0 |  | 0.5 | 0.6 |  | 0.8 | 66.8 | 16.8 |

TABLE I-continued

SYNTHESIS OF ETHYLENE GLYCOL FROM SYNGAS PLUS 1,3-DIOXOLANE[a]

| Example | 1,3-dioxolane (mmole) | Water (mmole) | Temp (°C.) | Pres. (psig) | ←Liquid Product Composition (Wt. %)→ | | | | | | | | |
|---|---|---|---|---|---|---|---|---|---|---|---|---|---|
| | | | | | H$_2$O | MeOH | EtOH | EGMME | EG | PG | DEG | Solvent | Dioxolane |
| X | 400 | 400 | 160 | 2700[b] | 19.8 | 1.7 | | 2.1 | 55.4 | 0.7 | 2.0 | 3.2 | 0.2 |
| | | | | | | 0.1 | | 0.2 | 0.2 | 0.2 | | 89.4 | 0.2 |
| XI | 200 | 200 | 180 | 5000 | 21.0 | 3.3 | 0.9 | 5.6 | 48.8 | 0.4 | 4.6 | 1.1 | 0.3 |
| | | | | | 0.2 | 0.2 | 0.1 | 0.6 | 0.3 | | 1.2 | 86.6 | 0.1 |
| XII | 200 | 200 | 180 | 5000[c] | 21.6 | 1.1 | 2.4 | 5.0 | 48.2 | 0.5 | 6.5 | 5.7 | 2.1 |
| | | | | | 0.2 | 0.5 | 0.8 | 0.1 | | | 2.8 | 83.7 | 0.8 |
| XIII | 200 | 200 | 180 | 8000 | 20.0 | 1.7 | 1.0 | 4.6 | 49.9 | 0.8 | 7.0 | 2.0 | 0.7 |
| | | | | | 0.1 | 0.1 | 0.1 | 0.3 | 0.3 | | 1.0 | 89.1 | 0.3 |

[a]Charge: Co, 12.0 mmole; Si, 24.0 mmole; Run Conditions CO/H$_2$, 1:2; 4 hours; constant pressure
[b]Initial Pressure
[c]Run for 18 hours Table II shows the volume of the liquid product in Examples II through XII. Also given is the ethylene glycol yield for each sample in mmoles.

TABLE II

| Example | Liquid Product Volume (ml) | Weight (g) | EG Yield (mmole) |
|---|---|---|---|
| II | 18 / 15 | 39.6 | 156 |
| III | 16 / 16 | 38.6 | 167 |
| IV | 9 / 21 | 36.1 | 47 |
| V | 19 / 15 | 39.7 | 151 |
| IV | 16 / 17 | 38.3 | 78 |
| VII | 11 / 22 | 38.1 | 40 |
| VIII | 17 / 16 | 38.8 | 166 |
| XI | 14 / 18 | 36.5 | 109 |
| X | 38 / 12 | 62.0 | 392 |
| XI | 19 / 17 | 41.4 | 149 |
| XII | 21 | | |
| XIII | 18 / 20 / 18 | 42.1 / 41.9 | 154 / 197 |

EXAMPLES XIV-XIX

Examples XIV through XIX were conducted in the same manner as Example I. The catalyst used in each case was dicobalt octacarbonyl and the promoter was triethylsilane. Different solvents were used and the effect upon ethylene glycol and total glycol production is shown in Table III, while Table IV illustrates the effect on liquid product volume/weight and gas composition.

It may be noted from an inspection of Tables III and IV that:

(a) Both chlorinated aromatic solvents, such as o-dichlorobenzene, and hydrocarbyl ether solvents, such as p-dioxane and anisole, are found to be effective for the production of ethylene glycol in good selectivity and yields from syngas plus 1,3-dioxolane.

(b) There appears to be very little competing water-gas shift or methanation activity with this class of solvent-solubilized, cobalt-silane catalyst.

(c) Ethylene glycol/methanol ratios in the crude liquid product phase may exceed 25:1 in some cases (e.g. Example XVII).

TABLE III

ETHYLENE GLYCOL SYNTHESIS FROM SYNGAS PLUS 1,3-DIOXOLANE

| Example | Solvent | 1,3-dioxolane (mmole) | Water (mmole) | Temp (°C.) | Pres. (psig) | ←Liquid Product Composition (Wt %)→ | | | | | | | | |
|---|---|---|---|---|---|---|---|---|---|---|---|---|---|---|
| | | | | | | H$_2$O | MeOH | EtOH | EGMME | EG | PG | DEG | Solvent | 1,3-Dioxolane |
| XIV | p-dioxane | 100 | 100 | 160 | 2700[b] | 8.9 | 0.9 | 0.6 | 3.4 | 13.3 | 0.2 | 8.4 | 61.3 | 0.2 |
| | | | | | | 0.5 | 0.2 | 0.1 | 0.3 | 0.2 | | 1.4 | 39.6 | 0.1 |
| XV | " | 200 | 200 | 160 | 2700[b] | 10.6 | 0.8 | | 0.6 | 30.7 | 0.2 | 4.1 | 48.0 | — |
| | | | | | | 0.4 | | | 0.3 | 0.4 | | 0.3 | 22/72 | — |
| XVI | Anisole | 100 | 100 | 160 | 2700[b] | 16.8 | 1.7 | 0.3 | 8.4 | 32.1 | 2.9 | 18.4 | 10.3 | 0.1 |
| | | | | | | 3.2 | 0.2 | | 0.1 | 0.3 | 0.2 | 0.7 | 82.4 | |
| XVII | Anisole | 200 | 200 | 160 | 2700[b] | 19.0 | 1.9 | 0.2 | 5.2 | 51.3 | 0.6 | 7.8 | 6.9 | — |
| | | | | | | 0.2 | 0.2 | | 0.7 | 0.9 | | 1.0 | 90 | |
| XVIII | Anisole | 200 | 200 | 160 | 2000[d] | 15.7 | 3.6 | 0.2 | 7.3 | 50.0 | 0.2 | 6.2 | 7.9 | 0.2 |
| | | | | | | 0.3 | 0.4 | | 1.2 | 0.9 | 0.2 | 0.7 | 90 | 0.2 |
| XIX | o-Dichloro- | 100 | 100 | 160 | 2700[b] | 14.5 | 2.6 | 0.3 | 7.5 | 45.0 | 0.6 | | 18.5 | 0.1 |

TABLE III-continued
ETHYLENE GLYCOL SYNTHESIS FROM SYNGAS PLUS 1,3-DIOXOLANE

| Example | Solvent | 1,3-dioxolane (mmole) | Water (mmole) | Temp (°C.) | Pres. (psig) | Liquid Product Composition (Wt %) | | | | | | | | |
|---|---|---|---|---|---|---|---|---|---|---|---|---|---|---|
| | | | | | | $H_2O$ | MeOH | EtOH | EGMME | EG | PG | DEG | Solvent | 1,3-Dioxolane |
| | benzene | | | | | 0.1 | 0.3 | | 0.9 | 0.7 | 0.2 | | 93 | — |

$^a$Charge: CO, 12.0 mmole, Si, 24.0 mmole; Run Conditions CO/$H_2$, 1:2; 4 hours
$^b$Initial Pressure
$^c$Not Determined
$^d$Constant Pressure
$^e$No Data

TABLE IV

| Liquid Product | | Gas Composition (%) | | | |
|---|---|---|---|---|---|
| Volume (ml) | Weight (g) | $H_2O$ | CO | $CO_2$ | $CH_4$ |
| $a$ | 31.8 | 67 | 33 | 0.1 | 0.1 |
| $a$ | | | | | |
| 37 / 3 | 43.0 | 65 | 35 | 0.1 | 0.1 |
| 11 / 20 | 31.6 | 67 | 33 | 0.1 | |
| 20 / 21 | 42.0 | 65 | 33 | | |
| 19 / 20 | 40.7 | 63 | 36 | | 0.1 |
| 9 / 17 | 30.2 | 63 | 33 | | |

$^a$Not Determined

EXAMPLE XX

A 450 ml-capacity reactor with a glass liner was charged with a mixture of dicobalt octacarbonyl (12.0 mmole Co, 2.052 g), triphenylsilane (24.0 mmole; 6.250 g) in 1,3-dioxolane (200 mmole, 14.82 g), water (200 mmole, 3.60 g) and 1,2,4-trichlorobenzene (15.0 g). The mixture was flushed with nitrogen, the reactor sealed, flushed with synthesis gas (CO/$H_2$, 1:2), pressured to 2000 psi with CO/$H_2$ (1:2) and heated to 180° C. with agitation. At temperature, the pressure was raised to 5000 psi with CO/$H_2$ (1:2) from a large surge tank. The pressure in the reactor was kept constant throughout the remainder of the run by incremental additions of CO/$H_2$ from the surge tank. After four hours, the reactor is allowed to cool, the gas pressure (3400 psig) noted, and the excess gas sampled and vented.

45.8 g of a two-phase liquid product was recovered. There was no solid precipitate at this stage.

Analysis of the less-dense liquid phase (18 ml) shows it to contain:
53.2 wt % ethylene glycol
7.5 wt % ethylene glycol monomethyl ether
0.5 wt % propylene glycol
8.9 wt % diethylene glycol
19.5 wt % water
2.3 wt % methanol
1.1 wt % ethanol
1.0 wt % 1,2,4-trichlorobenzene.

EXAMPLE XXI

Example XXI was conducted following the same procedure as Example XX. The only difference was that the promoter used was tetraethylenegermane. The reactor was charged with a mixture of dicobalt octacarbonyl (12.0 mmole Co, 2.052 g), tetraethylgermane (6.0 mmole, 1.133 g), in 1,3-dioxolane (200 mmole, 14.82 g) and 1,2,4-trichlorobenzene (15.0 g).

After reaction, 40.1 g of a two-phase liquid product was recovered. There was no solid precipitate at this stage.

Analysis of the less-dense liquid phase (20 ml) shows it to contain:
55.3 wt % ethylene glycol
6.2 wt % ethylene glycol monomethyl ether
0.5 wt % propylene glycol
5.9 wt % diethylene glycol
20.9 wt % water
2.6 wt % methanol
1.1 wt % ethanol
1.3 wt % 1,2,4-trichlorobenzene.

What is claimed is:

1. A process for making ethylene glycol comprising reacting synthesis gas, a mixture of carbon monoxide and hydrogen, plus 1,3-dioxolane in the presence of a catalyst containing an effective amount of cobalt-containing compound and a silane-containing promoter, selected from the group consisting of triethylsilane, triphenylsilane, hydroxytriphenylsilane, diphenylsilane, tricyclohexylsilane and tetramethylsilane, in a solvent selected from the group consisting of halogen-containing aromatic solvents from the group consisting of 1,2,4-trichlorobenzene, o-dichlorobenzene, bromobenzene, 1,3,5-tribromobenzene, p-bromotoluene, chlorobenzene and o-dibromobenzene, and hydrocarbyl ether solvents, at a temperature of at least 50° C., and a pressure of at least 500 psi.

2. The process of claim 1, wherein the molar ratio of cobalt-to-silane promoter is in the range from 1:0.1 to 1:100.

3. The process of claim 1, wherein the cobalt-containing compound is selected from the group consisting of cobalt oxides, cobalt salts of a mineral acid, cobalt salts of a carboxylic acid and cobalt carbonyl or hydrocarbonyl derivatives.

4. The process of claim 3, wherein the cobalt-containing compound is from the group consisting of dicobalt octacarbonyl, cobalt(II) oxide, cobalt(II) nitrate, cobalt(II) acetate or cobalt acetylacetonate.

5. The process of claim 4, wherein the cobalt-containing compound is dicobalt octacarbonyl.

6. The process of claim 1, wherein the silane promoter is selected from the group consisting of triethylsilane and triphenylsilane.

7. The process of claim 1, wherein the temperature is between 50° C. and 350° C.

8. The process of claim 1, wherein the temperature is between about 100° C. and 220° C.

9. The process of of claim 1, wherein the pressure is between 1000 psi and 6000 psi.

10. The process of claim 1, wherein the desired synthesis of ethylene glycol is conducted in the presence of a halogen-containing aromatic solvent selected from the group consisting of 1,2,4-trichlorobenzene, o-dichlorobenzene, bromobenzene, 1,3,5-tribromobenzene, p-bromotoluene, chlorobenzene and o-dibromobenzene.

11. The process of claim 1, wherein the desired synthesis of ethylene glycol is conducted in the presence of a hydrocarbyl ether solvent selected from the group consisting of p-dioxane and anisole.

12. A process for making ethylene glycol from synthesis gas, i.e., a mixture of carbon monoxide and hydrogen, and 1,3-dioxolane which comprises reacting said synthesis gas and 1,3-dioxolane in a liquid phase containing an effective amount of cobalt carbonyl compound and a silane containing promoter dispersed in a 1,2,4-tricholorobenzene solvent at a temperature of from about 100° C. to 220° C. and a pressure of from about 1000 psi to 6000 psi.

* * * * *